United States Patent [19]

Moreau et al.

[11] Patent Number: 5,015,419

[45] Date of Patent: May 14, 1991

[54] FATTY GLYCOLIC ACID DERIVATIVES AS YARN LUBRICANTS AND AS ANTIMICROBIAL AGENTS

[75] Inventors: Jerry P. Moreau; August V. Bailey, both of New Orleans; Anthony J. DeLucca, II, Metairie, all of La.

[73] Assignee: The United States of America as represented by the Secretary of Agriculture, Washington, D.C.

[21] Appl. No.: 261,531

[22] Filed: Oct. 24, 1988

[51] Int. Cl.$^5$ .................... C07C 69/66; C07C 69/675; C07C 69/73

[52] U.S. Cl. .................. 260/410.9 R; 8/115.6; 260/410.9 N; 514/547

[58] Field of Search ............. 260/410.9 N, 410.9 R, 260/410; 560/185, 266; 514/547

[56] References Cited

U.S. PATENT DOCUMENTS 2,608,577 8/1952 Weesner ..................... 560/185
3,383,313 5/1968 Hetchler ..................... 260/410.9 R
4,347,378 8/1982 Bailey et al. ..................... 560/105
4,464,392 8/1984 Bailey et al. ..................... 514/547
4,720,574 1/1988 Bailey et al. ..................... 560/185

OTHER PUBLICATIONS

A. V. Bailey et al., "Preparation of Some Fatty Glycolid Acid Derivatives and Screening for Antimicrobial Activity," J. Am. Oil Chem. Soc. 57(4): 139–141 (Apr. 1980).

A. Streitwieser, Jr. et al., "Introduction of Organic Chemistry," Macmillan Publishing, New York, 1976, pp. 681 and 685–687.

Primary Examiner—Vivian Garner
Attorney, Agent, or Firm—W. Howard Silverstein; John D. Fado; Randall E. Deck

[57] ABSTRACT

Diesters of glycolic acid are effective yarn lubricants for use in the textile industry. These compounds also inhibit the growth of bacteria and fungi.

12 Claims, No Drawings

FATTY GLYCOLIC ACID DERIVATIVES AS YARN LUBRICANTS AND AS ANTIMICROBIAL AGENTS

BACKGROUND OF THE INVENTION

1. Field of the Invention

This invention relates to novel glycolic acid fatty ester derivatives which are useful as yarn lubricants and antimicrobial agents.

2. Description of the Prior Art

Fiber lubricants, sometimes referred to as spinning oils or coning oils, are applied to textile fibers to facilitate handling of the yarn in operations such as spinning, weaving, knitting, etc. The lubricant helps prevent breakage of the fibers by the mechanical stress imposed by these operations.

A large number of chemical compositions have been used as textile lubricants. Cohen et al. U.S. Pat. No. 3,926,816 (1975) describe a representative group of lubricant formulation components including: phosphorylated oils, mixed alkylphosphate esters, amyl phenols, esters of castor oil, peanut oil, amines, mineral oil, glycerol esters, linoleic acid, oleic acid, polysiloxanes, etc. Desirable properties of fiber lubricants include lubricity, antistatic control, oxidation resistance, scourability, controlled viscosity range, nonallergenic, odor resistance, stability, corrosion resistance, and low volatility.

Often a single lubricant material will not have all the desirable or necessary properties, and other materials such as bactericides, antistatic agents, antioxidants, and stabilizers must be added to the formulation. See John Sylvester Olsen, U.S. Pat. No. 3,306,850 (1967).

Environmental considerations make it desirable to minimize the use of potentially toxic additives such as bactericides to textile products.

The germicidal activity of certain lipid compounds has long been known. Soap is a familiar example. Various fatty acids and their derivatives have found use as antiseptics and disinfectants, and also as preservatives for drugs and cosmetics. In recent times, however, the fatty acid-derived antimicrobials have to a considerable degree been replaced for such applications by more potent synthetic nonfatty compounds. More recently, many of the latter materials have come under suspicion by regulatory agencies because of their toxicity and side reactions. The pendulum is swinging back in favor of naturally occurring or derived lipid materials for application as antimicrobials and preservatives for food, pharmaceuticals, and other organic materials of commerce which are subject to bacterial or fungal attack, and in the formulation of self-preserving cosmetics.

In the search for antimicrobial agents for use in commercial products, it is necessary to ascertain the relative degree of inhibition that can be attained with any specific microorganisms under normal conditions of product use in accordance with the chemical and physical properties of the product. Minor differences in structure may result in one compound being inactive while a very similar compound has potent broad spectrum antimicrobial activity. Also, some compounds may be selectively active against only one or a small number of microorganisms, while another very similar compound shows a broad spectrum of activity against many types of organisms. Thus, screening is necessary in evaluating new compounds for potential use as antimicrobial agents, followed by intensive testing for specific end uses of those compounds found to have antimicrobial activity.

Bailey et al. U.S. Pat. No. 4,464,392 (1984) found that certain glycolic acid derivatives such as carboethoxymethyl hydrocinnamate and bis(carbomethoxymethyl)adipate were effective antimicrobial agents.

SUMMARY OF THE INVENTION

We have now discovered that mixed diesters derived from glycolic acid exhibit excellent yarn lubricant and antimicrobial properties.

It is an object of this invention to provide new lubricants derived from fatty compounds to facilitate the knitting process of yarns utilizing recent technological advances.

It is a further objective of this invention to provide new lubricant materials which have a good viscosity index and thus ensure uniform pickup over a wide range of use temperatures.

It is a further objective of this invention to provide new lubricant materials which have a wide range of antimicrobial activity, thus negating the additional use of special bactericides and fungicides.

Other objectives of this invention will in part be obvious and will in part appear hereinafter. We have unexpectedly discovered that the above and other objectives can be successfully achieved by utilization of the new fatty lubricants. We have discovered that these new fatty lubricants are essentially nonvolatile, odor resistant, corrosion resistant, and easily removable by any scouring or washing process. The properties which are imparted to the yarns by the fatty lubricant in addition to the aforementioned include a reduction of yarn to metal friction, an increase in yarn strength, and a decrease in the accumulation of static charge. A further advantage of this invention is the ability of application to the yarn by conventional equipment.

DESCRIPTION OF THE PREFERRED EMBODIMENT

The compounds that are the subject of this invention are certain long-chain fatty glycolic acid derivatives which are substituted at the hydroxyl and carboxyl functions and have the following structure:

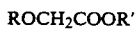

where R is an acyl group of from 16 to 22 carbon atoms and R' is an alkyl or alkenyl group of from 4 to 22 carbon atoms. R and R' may be straight chain or branched, saturated, monounsaturated, or polyunsaturated.

In the preparation of the fatty glycolic acid lubricant materials in this invention, any fatty acid alcohol saturated or unsaturated having 4 to 22 carbon atoms or mixtures thereof may be used. The fatty alcohols used in this invention include such alcohols as butyl, ethylhexyl, octyl, decyl, hexadecyl, 11-eicosenyl, and erucyl. Likewise, any fatty acid saturated or unsaturated and/or branched or unbranched may be used. The fatty acids used in the preparation were, for example, palmitoleic, oleic, petroselinic, erucic, and composite soybean oil fatty acids.

Soybean oil has the following fatty acid composition as indicated in Bull. 1170, "Composition and Constants, Natural Fats and Oils," Ashland Chemical Co.

| | Percent |
|---|---|
| Myristic acid | 0.1 |

| -continued | |
|---|---|
| | Percent |
| Palmitic acid | 10.5 |
| Stearic acid | 3.2 |
| Oleic acid | 22.3 |
| Linoleic acid | 54.5 |
| Linolenic acid | 8.3 |
| Arachidic acid | 0.2 |
| Eicosenoic acid | 0.9 | inert carrier such as a nonvolatile organic liquid for application. Another possible means of application is by forming a water-based emulsion of the lubricant. Other modes of application will be obvious to those skilled in the art.

It also will be evident to those skilled in the art that small amounts of other ingredients may be added to the lubricant composition of this invention. For example, small amounts of

TABLE I

Properties of Glycolic Esters

| No. | Compound | Density$^a$ | Ref. Index$^b$ | Viscosity$^c$ |
|---|---|---|---|---|
| 1. | Carbobutoxymethyl erucate | 0.9100 | 1.4527 | 176.1 |
| 2. | Carbooctyloxymethyl erucate | 0.8786 | 1.4517 | 158.7 |
| 3. | Carbo-2-ethylhexyloxymethyl erucate | 0.8956 | 1.4638 | 160.2 |
| 4. | Carbodecyloxymethyl erucate | 0.8982 | 1.4532 | 165.2 |
| 5. | Carbohexadecyloxymethyl erucate | (solid: mp 68 C) | | |
| 6. | Carbo-11-eicosenyloxymethyl erucate | 0.8452 | 1.4631 | 159.7 |
| 7. | Carboerucyloxymethyl erucate | 0.8808 | 1.4616 | 155.7 |
| 8. | Carboerucyloxymethyl palmitoleate | (solid: mp 30 C) | | |
| 9. | Carboerucyloxymethyl oleate | 0.8763 | 1.4595 | 167.8 |
| 10. | Carboerucyloxymethyl petroselinate | 0.8822 | 1.4595 | 154.1 |

$^a d_4^{30}$
$^b n_D^{30}$
$^c$Kinematic index values

The compounds of this invention may be prepared by a variety of synthetic procedures. However, it was discovered that the following method of synthesis may be used to advantage.

The reaction scheme is particularly efficient in that the glycolic acid (normally containing 30% water) is added dropwise to a molecular equivalent of an alcohol, such as those mentioned above, which has been heated at reflux in combination with an excess of benzene containing a catalytic amount of p-toluene sulfonic acid. During continued reflux, contaminant water from the glycolic acid and water by-product from the reaction is azeotropically distilled and collected in a Dean-Stark trap. The reaction is considered completed when an equivalent amount of water has been collected and no additional water is distilled over. The glycolic acid ester is recovered by a simple washing procedure in a separatory funnel to remove any unreacted glycolic acid and the acid catalyst. The pure product is obtained by a short pass distillation to remove it from any unreacted alcohol and any polymer which might have formed in the course of the reaction. To the isolated glycolate is added an equivalent weight of an acyl chloride of one of the aforementioned fatty acids in five volumes of anhydrous benzene containing an equivalent plus 10% excess of dry pyridine as the acid scavenger. After the heat of reaction is dissipated, the pyridine hydrochloride is filtered off and the solution is successively washed with aqueous HCl followed with water until free of mineral acid. The solvent is removed and the product recovered. The chemical structure of the long-chain fatty acid glycolate thus obtained was determined by infrared spectroscopy and nuclear magnetic resonance analyses. Properties of the acyl glycolic acid esters thus produced are shown in Table I.

It will be obvious to those skilled in the art that the lubricants described herein may be used neat as lubricants on the fibers or they may be combined with an inert carrier such as a nonvolatile organic liquid for application. Another possible means of application is by forming a water-based emulsion of the lubricant. Other modes of application will be obvious to those skilled in the art.

It also will be evident to those skilled in the art that small amounts of other ingredients may be added to the lubricant composition of this invention. For example, small amounts of surfactants, antistatic agents, antioxidants, emulsion stabilizers, and the like may be added as desired. Those skilled in the art will be able to establish the requirements for particular formulations with only minimal, routine experimentation.

The lubricants of this invention may be applied to yarns by conventional techniques. A particularly advantageous method of application is the Kiss-Roll technique as described in Textile Chemist and Colorist, Vol. 16, No. 8, pp. 131-143 (1984). Yarn lubricity was determined by the coefficient of friction (cf) evaluation by ASTM method D3108-83. The lower the cf value the better the lubricant.

In general, add-on was inversely proportionate to viscosity of formulations containing the same chemical composition. That is, the lower viscosity formulations tended to give greater penetration into the yarn compared to the higher viscosity formulations, while maintaining other processing variables. However, in the evaluation of these various lubricants, viscosity alone was not the only determining factor for add-on, as shown in Table II.

Yarn lubricants are generally applied at low add-ons. A topical or surface treatment is all that is required to obtain desired frictional properties.

To determine if the weight of lubricant added would affect the frictional properties, carbooctyloxymethyl erucate was used to treat bleached and dyed yarns at various levels of add-on, and the cf was determined. The data, shown in Table III, indicate that the cf values for dyed yarns increased slightly with increasing amounts of add-on but leveled off at 0.7% add-on. This indicates that there is a point at which additional add-on does not contribute additional benefit to the frictional properties of treated yarn. This optimum add-on may vary for each lubricant, but if a lubricant is to have any effect on the frictional properties of a particular type of yarn it will, in most cases, manifest itself at low levels of add-on. This

TABLE II

Comparison of Lubricant Viscosity and Add-On

| Lubricant | Viscosity (cps) | Bleached Yarn % Add-On | cf[a] | Dyed Yarn % Add-On | cf[a] |
|---|---|---|---|---|---|
| Lubritol (petroleum oil, vegetable oil, emulsifiable wax, and surfactant) | 6 | 0.5 | 0.26 | 0.7 | 0.28 |
| Lubrol NF-783 (butyl stearate, ethoxylated alcohols and long-chain fatty acids) | 22 | 0.4 | 0.26 | 0.5 | 0.25 |
| SSC-6X (mineral oil, fatty acids, phosphate esters) | 32 | 0.4 | 0.25 | 0.5 | 0.27 |
| Fisher (light weight mineral oil) | 50 | 0.7 | 0.30 | 1.2 | 0.30 |
| Carbobutoxymethyl erucate | 28 | 1.1 | 0.25 | 0.9 | 0.26 |
| Carbooctyloxymethyl erucate | 28 | 0.4 | 0.24 | 0.7 | 0.26 |
| Carbodecyloxymethyl erucate | 28 | 0.8 | 0.21 | 1.2 | 0.23 |
| Carbo-2-ethylhexyloxymethyl erucate | 28 | 1.5 | 0.29 | 0.5 | 0.29 |

[a]Coefficients of friction of untreated gray, bleached, and dyed yarns were 0.27, 0.30, 0.60, respectively.

TABLE III

Effect of Add-On and Yarn Lubricity

| Bleached Yarn % Add-On[a] | cf[b] | Dyed Yarn % Add-On | cf |
|---|---|---|---|
| 0.37 | 0.24 | 0.40 | 0.28 |
| 0.49 | 0.24 | 0.42 | 0.28 |
| 0.51 | 0.23 | 0.70 | 0.26 |
| 0.64 | 0.23 | 1.10 | 0.26 |

[a]Glycolate $C_8$ lubricant
[b]Coefficient of friction of untreated yarns 0.30 and 0.60, respectively.

is most evident by the decrease in cf of untreated (0.60) to treated (0.28) dyed yarn with only 0.4% add-on.

The data shown in Table IV indicate that slightly better cf values were obtained for the glycolate derivative containing the $C_{10}$ alcohol function. The bulkier branched chain $C_8$ derivative gave slightly higher cf values than the straight chain glycolates.

Bleached and dyed yarns are difficult to knit because the natural waxes had been removed during wet processing, thus reducing lubricity. A lubricating oil must therefore be added to reduce friction in order to improve knitting efficiency. Dyed yarn is the most difficult to knit, as indicated by the cf value of 0.60. Approximately 14,000 yds of yarn were treated with carbooctyloxymethyl erucate. The effectiveness of this glycolate as a lubricant for knitting yarn was evaluated by determination of the quality of fabrics produced at various knitting speeds on the knitting machine. The dyed yarn treated with the fatty glycolate derivative was knitted at maximum speed to produce a quality fabric without holes. Conversely, when the untreated dyed yarn was knitted at medium speed, large holes and sometimes even large gaps occurred in the knitted fabric. Fabric integrity could be achieved only when the untreated yarn was knitted at minimum speed. However, even under these conditions, several holes occurred throughout the fabric.

These glycolate ester lubricants might also be utilized in weaving as well as knitting. In weaving operations the warp yarns are subjected to considerable abrasive action and require a sizing treatment (called slashing) to reduce yarn breaks and thereby increase efficiency in fabric production. Slashing in general consists of treating the gray yarns with a sizing agent (i.e., starch or polyvinyl alcohol) to give it added abrasion resistance, strength, and reduced hairiness.

Traditionally, these sizing formulations are washed from the woven fabric before further processing because they can interfere

TABLE IV

Properties of Lubricant-Treated Yarns

| Example | Compound | Bleached % Add-On | cf[a] | Dyed % Add-On | cf |
|---|---|---|---|---|---|
| 1. | Carbobutyloxymethyl erucate | 1.1 | 0.25 | 0.9 | 0.26 |
| 2. | Carbooctyloxymethyl erucate | 0.4 | 0.24 | 0.7 | 0.26 |
| 3. | Carbo-2-ethylhexyloxymethyl erucate | 1.5 | 0.29 | 0.5 | 0.29 |
| 4. | Carbodecyloxymethyl erucate | 0.8 | 0.21 | 1.2 | 0.23 |
| 5. | Carbohexadecyloxymethyl erucate | 0.7 | 0.25 | 1.1 | 0.24 |
| 6. | Carbo-11-eicosenyloxymethyl erucate | 0.9 | 0.24 | 0.8 | 0.26 |
| 7. | Carboerucyloxymethyl erucate | 0.6 | 0.28 | 0.7 | 0.27 |
| 8. | Carboerucyloxymethyl palmitoleate | 1.1 | 0.27 | 1.0 | 0.27 |
| 9. | Carboerucyloxymethyl oleate | 0.4 | 0.24 | 0.6 | 0.23 |
| 10. | Carboerucyloxymethyl petroselinate | 0.6 | 0.26 | 0.9 | 0.26 |
| 11. | Carbodecyloxymethyl (whole soybean acids)-ate | 0.8 | 0.29 | 0.8 | 0.28 |
| 12. | Carboerucyloxymethyl (whole soybean acids)-ate | 0.7 | 0.27 | 1.1 | 0.29 |
| | SSC-6X (Fatty acids, mineral oil, phosphate esters)[b] | 0.4 | 0.25 | 0.5 | 0.27 |
| | Fisher (Lightweight mineral oil)[b] | 0.7 | 0.30 | 1.2 | 0.30 |
| | Lubritol (Petroleum oil, vegetable oil, waxes)[b] | 0.5 | 0.26 | 0.7 | 0.28 |
| | Lubrol NF-783 (Butyl stearate, ethoxylated alcohol, fatty acids)[b] | 0.4 | 0.26 | 0.5 | 0.25 |
| | Untreated control | | 0.30 | | 0.60 |

[a]cf = Coefficient of friction
[b]Commercial lubricant with dyeing and/or finishing. Gray yarns, which naturally contain waxes, have the necessary lubricity but lack the required abrasion resistance, strength, and smoothness for weaving. Polymeric sizing treatments increase the yarn abrasion resistance, increase the breaking strength, and increase the yarn's smoothness by reducing its hairiness. However, these polymer treatments reduced the yarn's lubricity. A technique sometimes used in slashing is to incorporate low-melting solid waxes into the sizing formulation or to apply the hot wax as a topping (overcoat) treatment to increase yarn lubricity. Similarly, topping with a small amount of glycolate ester lubricant offers a means for improving the lubricity of polymer-sized yarns.

Table V shows the cf values for four gray yarns that were sized with four polymer formulations and topped with carbodecyloxymethyl erucate lubricant. The polymer formulations represent a cross section of the polyacrylates and polyurethanes used in the sizing investigation. As shown in the table, the cf values increased from 0.27 for the gray yarn to 0.32-0.34 after polymer sizing. After topping with the glycolate lubricant the cf values were reduced, in most cases, to levels even below that of the unsized yarn. Although there are numerous factors that can affect the weaving performance of a yarn, the increased lubricity as reflected in the lower cf values can be expected to greatly facilitate the weaving of polymer-sized yarns.

Biological activity of the new lubricant compounds was established by in vitro tests against bacteria, and fungi.

The following examples are given to further illustrate the invention. They are intended to limit the scope of the invention, which is defined by the claims.

TABLE V

Effect of Lubricant Topping[a] of Sized Yarn

| Polymer Treatment[b] | Original cf[c] | Topped With Glycolate Ester cf |
|---|---|---|
| A1 | 0.34 | 0.25 |
| A2:U1 (3:1) | 0.34 | 0.21 |
| A2 | 0.32 | 0.24 |
| A1:U1 (1:3) | 0.34 | 0.28 |

[a]Carbodecyloxymethyl erucate
[b]Moreau, J. P., J. Coated Fabrics 13: 258-269 (1984)
A1 = polyacrylate; glass transition temperature (Tg) = 0C
A2 = polyacrylate; Tg = 33° C.
U1 = polyurethane; film forming temperature (Tf) = 28° C.
[c]Untreated gray yarn, cf - 0.27

EXAMPLE 1

Carbobutyloxymethyl Erucate

To 101 g (1.5 moles) of butyl alcohol containing 5 g of p-toluene sulfonic acid in 325 ml of benzene at reflux was added dropwise 150 g (ca. 1.5 moles acid) of 70% glycolic acid. The flask was equipped with a Dean-Stark trap to collect the 30% of water from the aqueous glycolic acid mixture and to collect the 27 g (1.5 moles) of water liberated during the reaction—a total of ca. 68 ml. The benzene solution of the product was water washed and dried over anhydrous sodium sulfate. The benzene was stripped off on a rotary evaporator. A short pass distillation at reduced pressure produced a good grade butyl glycolate. The structure was established by infrared and nuclear magnetic resonance spectroscopy.

To 65 g (0.5 moles) of butyl glycolate in a benzene solution containing 30 ml of anhydrous pyridine was added dropwise with stirring 179 g (0.5 moles) of erucyl chloride. The precipitated pyridine chloride was filtered, washed with benzene, and discarded. The benzene was stripped off on a rotary evaporator. The yield of product was essentially quantitative. Its structure was established by infrared and nuclear magnetic resonance spectroscopy. It had $n_D^{30}$ 1.4527, and $d_4^{30}$ 0.9100, and a viscosity index of 176.1.

EXAMPLE 2

Carbooctyloxymethyl Erucate

This compound was prepared by the procedure of Example 1. Two hundred grams (1.5 moles) of octyl alcohol and 150 g (1.5 moles acid) of 70% glycolic acid were used to prepare the octyl glycolate. Eighty-four grams (0.5 moles) of octyl glycolate and 179 g (0.5 moles) erucoyl chloride were used to prepare the named compound. Its structure was established by infrared and nuclear magnetic resonance spectroscopy. It had $n_D^{30}$ 1.4517, $d_4^{30}$ 0.8786, and a viscosity index of 158.7.

EXAMPLE 3

Carbo-2-ethylhexyloxymethyl Erucate

This compound was prepared by the procedure of Example 1. Two hundred grams (1.5 moles) of ethylhexyl alcohol and 150 g (1.5 moles acid) of 70% glycolic acid were used to prepare the ethylhexyl glycolate, and 179 g (0.5 moles) erucoylchloride were used to prepare the named compound. Its structure was established by infrared and nuclear magnetic resonance spectroscopy. It had $n_D^{30}$ 1.4638 and $d_4^{30}$ 0.8956, and a viscosity index of 160.2.

EXAMPLE 4

Carbodecyloxymethyl Erucate

This compound was prepared by the procedure of Example 1. Two hundred thirty-seven grams (1.5 moles) of decyl alcohol and 150 g (1.5 moles acid) of 70% glycolic acid were used to prepare the decyl glycolate. One hundred forty-eight grams (0.5 moles) of decyl glycolate and 179 g (0.5 moles) erucoyl chloride were used to prepare the named compound. Its structure was established by infrared and nuclear magnetic resonance spectroscopy. It has $n_D^{30}$ 1.4532, $d_4^{30}$ 0.8982, and a viscosity of 165.2.

EXAMPLE 5

Carbohexadecyloxymethyl Erucate

This compound was prepared by the procedure of Example 1. One hundred ninety-four grams (0.8 moles) of hexadecyl alcohol and 80 g (0.8 moles acid) of 70% glycolic acid were used to prepare the hexadecyl glycolate. One hundred fifty grams (0.5 moles) of hexadecyl glycolate and 179 g (0.5 moles) of erucoyl chloride were used to prepare the named compound. Its structure was established by infrared and nuclear magnetic resonance spectroscopy. It was a solid with a mp=68° C.

EXAMPLE 6

Carbo-11-eicosenyloxymethyl Erucate

This compound was prepared by the procedure of Example 1. One hundred forty-eight grams (0.5 moles) of eicosenol and 50 g (0.5 moles acid) of 70% glycolic acid were used in the preparation of eicosenyl glycolate. One hundred seventy-seven grams (0.5 moles) of eicosenyl glycolate and 179 g (0.5 moles) of erucoyl chloride were used to prepare the named compound. Its structure was established by infrared and nuclear magnetic resonance spectroscopy. It had $n_D^{30}$ 1.4631, $n_4^{30}$ 0.8452, and a viscosity index of 159.7.

EXAMPLE 7

Carboerucyloxymethyl Erucate

This compound was prepared by the procedure of Example 1. One hundred sixty-two grams (0.5 moles) of erucyl alcohol and 50 g (0.5 moles acid) of 70% glycolic acid were used to prepare erucyl glycolate. One hundred ninety-one grams (0.5 moles) of erucyl glycolate and 179 g (0.5 moles) of erucoyl chloride were used to prepare the named compound. The structure was established by infrared and nuclear magnetic resonance spectroscopy. It had $n_D^{30}$ 1.4616, $d_4^{30}$ 0.8808, and a viscosity index of 155.7.

EXAMPLE 8

Carboerucyloxymethyl Palmitoleate

This compound was prepared by the procedure of Example 1. One hundred sixty-two grams (0.5 moles) of erucyl alcohol and 50 ml (0.5 moles acid) of 70% glycolic acid were used to prepare the erucyl glycolate. Ninety-five grams (0.25 moles) of erucyl glycolate and 68 g (0.25 moles) of palmitoleoyl chloride were used to prepare the named compound. The structure was established by infrared and nuclear magnetic resonance spectroscopy. It was a solid with a mp=30° C.

EXAMPLE 9

Carboerucyloxymethyl Oleate

This compound was prepared by the procedure of Example 1. One hundred sixty-two grams (0.5 moles) of erucyl alcohol and 50 g (0.5 moles acid) of 70% glycolic acid were used to prepare erucyl glycolate. Ninety-five grams (0.25 moles) of erucoyl glycolate and 75 g (0.25 moles) of oleoyl chloride were used to prepare the named compound. The structure was established by infrared and nuclear magnetic resonance spectroscopy. It had $n_D^{30}$ 1.4595, $d_4^{30}$ 0.8763, and a viscosity index of 167.8.

EXAMPLE 10

Carboerucyloxymethyl Petroselinate

This compound was prepared by the procedure of Example 1. One hundred sixty-two grams (0.5 moles) of erucyl alcohol and 50 g (0.5 moles acid) of 70% glycolic acid were used to prepare erucyl glycolate. Ninety-five grams (0.25 moles) erucyl glycolate and 75 g (0.25 moles) of petroselinoyl chloride were used to prepare the named compound. The structure was established by infrared and nuclear magnetic resonance spectroscopy. It had $n_D^{30}$ 1.4595, $d_4^{30}$ 0.8822, and a viscosity index of 154.1.

EXAMPLE 11

Carbodecyloxymethyl (Whole Soybean Acids)-ate

The compound was prepared by the procedure of Example 1. Two hundred thirty-seven grams (0.5 moles) of decyl alcohol and 50 g (0.5 moles acid) of 70% glycolic acid were used to prepare the decyl glycolate. One hundred forty-eight grams (0.5 moles) of decyl glycolate and 150 g (0.5 moles) of whole soybean fatty acid chlorides were used to prepare the named compound. The structure was established by infrared spectroscopy.

EXAMPLE 12

Carboerucyloxymethyl (Whole Soybean Acids)-ate

This compound was prepared by the procedure of Example 1. One hundred sixty-two grams (0.5 moles) of erucyl alcohol and 50 g (0.5 moles acid) of 70% glycolic acid were used to prepare erucyl glycolate. Ninety-five grams (0.25 moles) of erucyl glycolate and 75 g (0.25 moles) of whole soybean fatty acid chlorides were used to prepare the named compounds. The structure was established by infrared spectroscopy.

EXAMPLE 13

Application of Lubricant to Yarns

The yarn used for this invention was a 30/1 ring spun carded 100% cotton with a 4.2 twist multiplier. Bleached yarns were prepared as follows: One-pound packages of yarn were prepared on dye tubes. These were processed in a Gaston County 6-lb-package dye machine. The yarns were scoured with 2% sodium hydroxide and 0.1% wetting agent and 0.5% of sequestering agent at 85°–95° C. for 20 min. The yarn packages were bleached in a solution of: 3.2% hydrogen peroxide, 1.6% sodium silicate, and 0.4% sequestering agent. The pH was adjusted to 10.5 with sodium hydroxide and the yarn was bleached for 75 min at 85° C. The yarn was given a mild acetic acid scouring then rinsed thoroughly. Dyed yarns were prepared from the above bleached yarns. Procion Brilliant Orange N-2R (Reactive Orange 4) dye was used according to specifications from Imperial Chemical Industries, Ltd. Oils were applied to the yarn on a laboratory single-end-slasher by a kiss-roll technique. A 1.5 inch diameter roll was used in which surface speed was varied to obtain the desired oil pickup. Yarn speed was maintained at approximately 16.5 m/min. Add-on was determined by weight difference at standardized conditions (70° F. and 65% RH) before and after treatment.

EXAMPLE 14

Evaluation of Lubricant-Treated Yarn

Yarn lubricity was determined by coefficient of friction evaluation using ASTM Method D3108-83 [American Society for Testing and Materials, Vol. 07.01, Method D3108-83, Philadelphia, Pa. (1876)] at a wrap angle of 180 degrees and a speed of 100 m/min. In most test series, input tension was maintained at 20 grams-force.

Untreated gray cotton yarns and yarns treated with the new lubricant compounds were knitted at maximum speed. The untreated yarns when knitted resulted in fabrics with large holes, and in some cases there were large gaps in the fabric production due to yarn breakage. Yarns treated with the new lubricants when knitted at maximum speed produced good quality fabrics without any holes or gaps in the fabric production.

Properties of lubricant-treated yarns are shown in Table IV.

EXAMPLE 15

Antimicrobial Activity of Lubricants

The bioactivity of these new compounds was established in vitro and relates to the growth inhibition of bacteria, and fungi.

The microorganisms used were obtained from stock cultures. Difco dehydrated mycological agar at pH 7.0 was used to test the inhibition of the test fungus by the compounds. Difco nutrient was used to grow the bacteria and yeast cultures.

The compounds were screened for their antimicrobial activity against two bacteria--a gram positive, *Staphylococcus aureus*; a gram negative, *Escherichia coli*; a yeast, *Candida utilis*; and a fungus, *Penicillium notatum*.

Spread agar plates were used to measure the antimicrobial activity against bacteria and yeast.

Filter paper discs 6.5 mm in diameter, made from Whatman Number 1 filter paper, were wetted until they were completely saturated with the compound being tested, and the wetted discs were placed on the surface of the agar plates inoculated with the test organisms.

A minimum of three experiments at different times, employing duplicate plates, were made for each compound under test.

All test plates were incubated at the optimum growing temperature for each organism, and readings were taken after 24, 48, 72, and 120 hour periods.

Results of the antimicrobial tests are shown in Table VI.

wherein R is a fatty acid acyl group of from 16 to 22 carbon atoms and may be straight chain or branched, saturated, monounsaturated or polyunsaturated, and R' is an alkyl or alkenyl group of from 4 to 22 carbon atoms.

2. A glycolic acid ester as described in claim 1 wherein R' is butyl and R is erucoyl.

3. A glycolic acid ester as described in claim 1 wherein R' is octyl and R is erucoyl.

4. A glycolic acid ester as described in claim 1 wherein R' is 2-ethylhexyl and R is erucoyl.

5. A glycolic acid ester as described in claim 1 wherein R' is decyl and R is erucoyl.

6. A glycolic acid ester as described in claim 1 wherein R' is hexadecyl and R is erucoyl.

7. A glycolic acid ester as described in claim 1 wherein R' is 11-eicosenyl and R is erucoyl.

8. A glycolic acid ester as described in claim 1 wherein R' is erucyl and R is erucoyl.

9. A glycolic acid ester as described in claim 1 where R' is erucyl and R is palmitoleoyl.

10. A glycolic acid ester as described in claim 1 wherein R' is erucyl and R is oleoyl.

TABLE VI

| | | Antimicrobial Activity[a] Against Selected Microorganism[b] | | | |
|---|---|---|---|---|---|
| Example | Compound | A | B | C | D |
| 1. | Carbobutyloxymethyl erucate | 00 | 0 | 00 | 00 |
| 2. | Carbooctyloxymethyl erucate | 00 | + | 0 | + |
| 3. | Carbo-2-ethylhexyloxymethyl erucate | 00 | + | 00 | + |
| 4. | Carbodecyloxymethyl erucate | 00 | 0 | 0 | 00 |
| 5. | Carbohexadecyloxymethyl erucate | 00 | 00 | 00 | 00 |
| 6. | Carbo-11-eicosenyloxymethyl erucate | 00 | 0 | 00 | 0 |
| 7. | Carboerucyloxymethyl erucate | 00 | 0 | 0 | 00 |
| 8. | Carboerucyloxymethyl palmitoleate | 00 | 0 | 0 | 00 |
| 9. | Carboerucyloxymethyl oleate | 00 | 00 | + | 00 |
| 10. | Carboerucyloxymethyl petroselinate | 00 | 0 | 00 | 00 |
| 11. | Carbodecyloxymethyl (whole soybean acids)-ate | + | + | + | + |
| 12. | Carboerucyloxymethyl (whole soybean acids)-ate | 00 | 00 | 00 | 00 |
| Control[c] | | 00 | 0 | 0 | 0 |

[a] + = Zone of inhibition less than 5 mm beyond disc of cylinder area at 120 hr.
00 = Organism failed to grow on disc or cylinder area at 120 hr.
0 = Slight growth on the disc or cylinder area at 120 hr.
[b] A = *Escherichia coli*; B = *Candida utilis*; C = *Staphylococcus aureus*; D = *Penicillium notatum*.
[c] Phosphate buffer with 0.2% peptone, pH 7.0.

We claim:

1. Glycolic acid esters of the formula:

ROCH$_2$COOR'

11. A glycolic acid ester as described in claim 1 wherein R' is erucyl and R is petroselinoyl.

12. A glycolic acid ester as described in claim 1 wherein R' is erucyl and R is a mixture of acyl groups derived from whole soybean acids.

* * * * *